United States Patent [19]

Wolfe

[11] Patent Number: 4,689,010

[45] Date of Patent: Aug. 25, 1987

[54] DENTAL IMPRESSION TRAY

[75] Inventor: Herbert Wolfe, Pomona, N.Y.

[73] Assignee: Sultan Dental Products, Ltd., Englewood, N.J.

[21] Appl. No.: 820,138

[22] Filed: Jan. 21, 1986

[51] Int. Cl.[4] ............................................... A61C 9/00
[52] U.S. Cl. ..................................................... 433/38
[58] Field of Search ................................... 433/37, 38

[56] References Cited

U.S. PATENT DOCUMENTS 4,439,151 3/1984 Whelan .................................. 433/74

Primary Examiner—Robert Peshock
Attorney, Agent, or Firm—Steinberg & Raskin

[57] ABSTRACT

A dental impression tray includes a tray portion anatomically contoured to fit over at least a part of a patient's upper and/or lower dentition of which an impression is to be obtained. The tray portion is loaded with impression material and situated opposite to the desired dentition part whereupon the patient bites into the soft impression material to form an impression of the dentition in the material. The tray portion is defined by at least one wall on which a plurality of vertically extending adjacent ribs are integrally formed defining a plurality of channels therebetween into which the impression material flows. The ribs have a dovetail cross-section so that the channels narrow or converge in the inward direction, i.e. towards the interior of the tray portion, to prevent the impression material from separating from the side wall in the inward direction as well as spreading laterally as and after the impression is taken to thereby provide a precise impression of the dentition. Each rib may be provided with a lower surface situated within the tray portion under which the impression material flows when the tray is loaded with impression material to prevent the impression material from lifting out of the tray, i.e. moving in the vertical direction with respect to the side wall, when the teeth are removed from the impression material.

9 Claims, 9 Drawing Figures

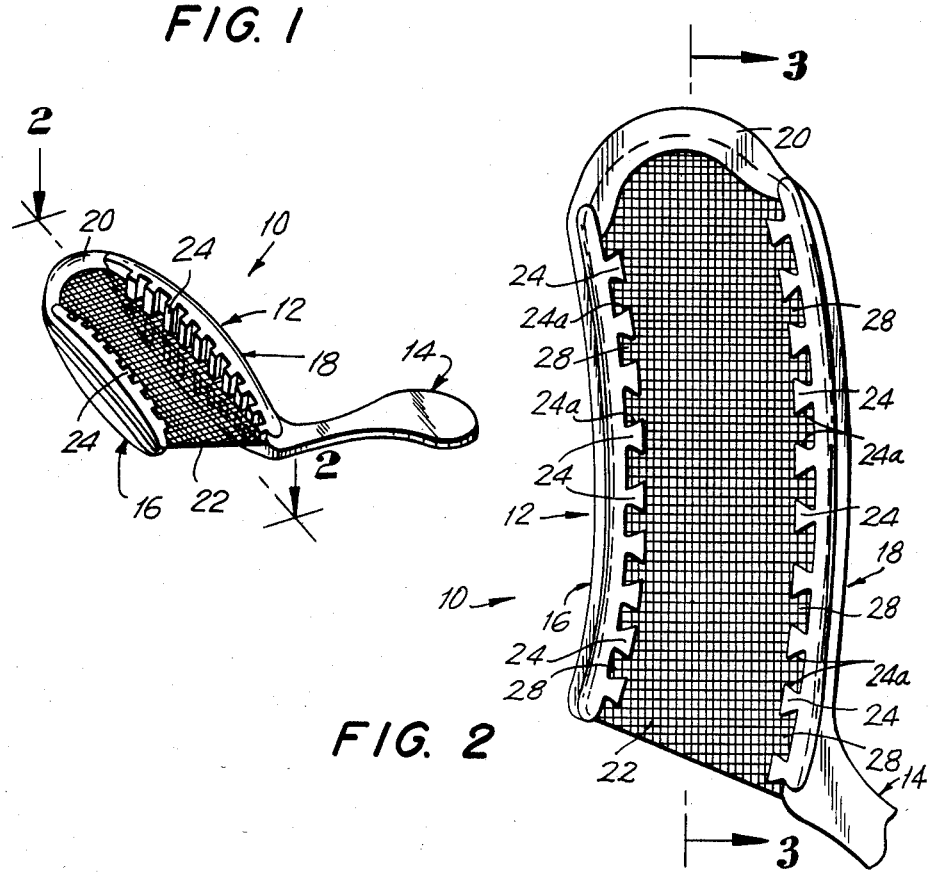
FIG. 1
FIG. 2
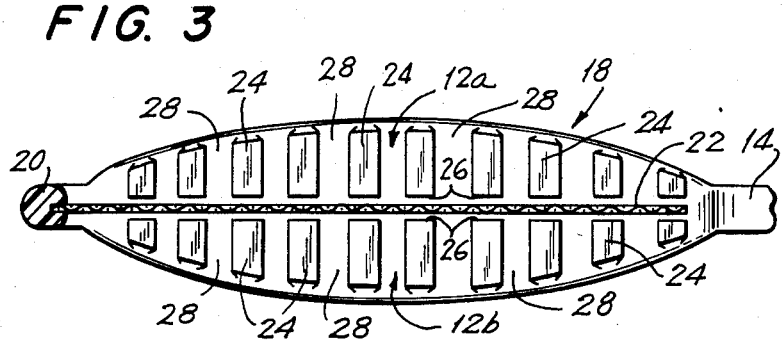
FIG. 3

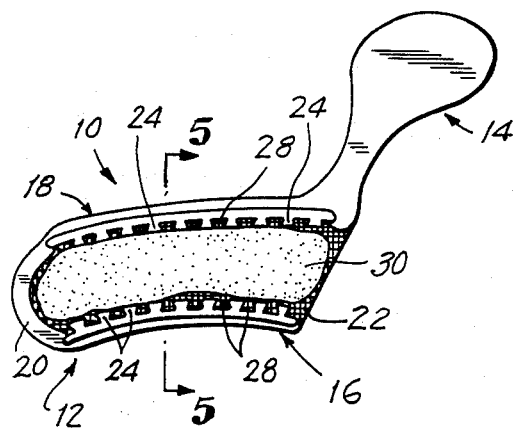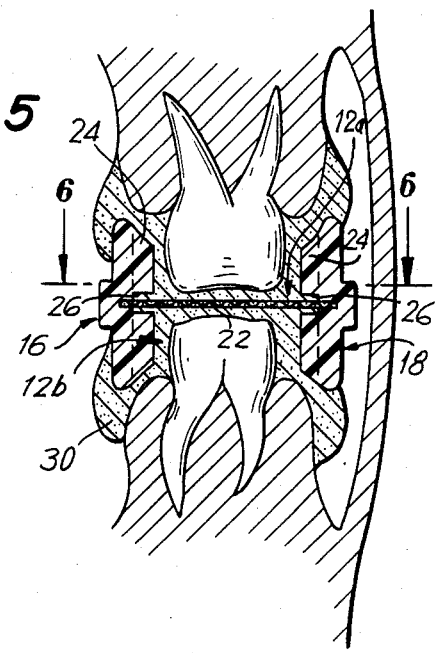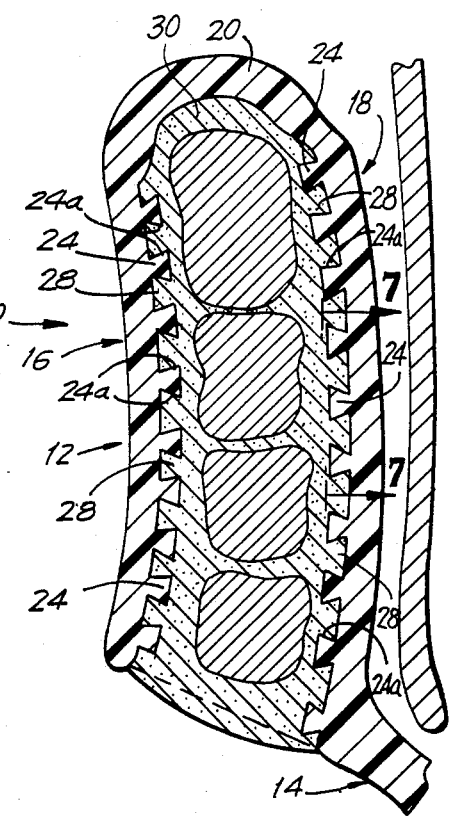

FIG. 7
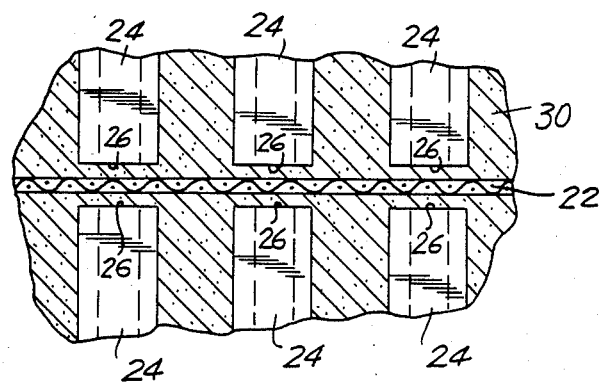
FIG. 8
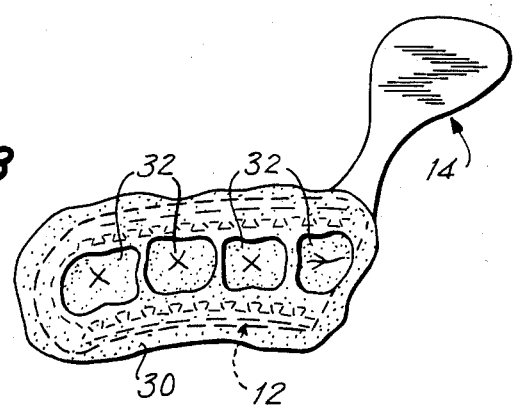
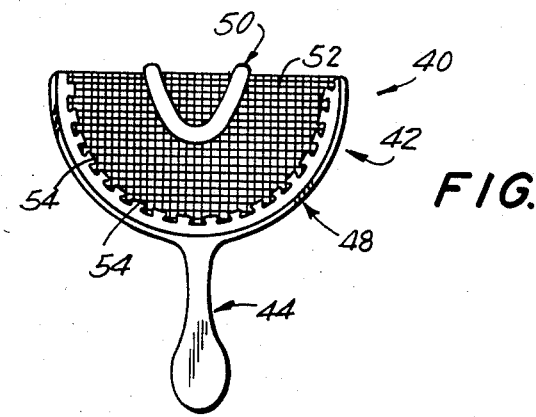
FIG. 9

DENTAL IMPRESSION TRAY

BACKGROUND OF THE INVENTION

This invention relates generally to dental instruments and, more particularly, to trays for obtaining an impression of a patient's dentition.

Dental trays for obtaining an impression of a patient's dentition are known. Such trays generally include a tray portion anatomically contoured to fit over at least a part of a patient's upper and/or lower dentition of which an impression is to be obtained. The tray portion is loaded with a suitable settable impression material and situated opposite to the desired dentition part whereupon the patient bites into the impression material to form an impression of the dentition in the material. After the impression material sets, it is used as a mold into which plaster can be poured which, upon setting, forms a model of the dentition.

A problem encountered in the use of conventional dental impression trays is that as and after the impression is taken and before the impression material has set, the impression material tends to move with respect to the wall or walls defining the tray portion. In particular, as the impression is being taken, the soft impression material tends to separate from the wall and move inwardly into the tray portion and also tends to spread laterally along the wall. Moreover, after the impression is taken, the impression material tends to lift out of the tray as the patient's teeth are removed from the impression material. Such movement of the impression material detracts from the precision of the impression obtained.

Attempts have been made to prevent the soft impression material from moving in the manner described above. For example, impression adhesives are available which are applied to the tray wall prior to the tray portion being loaded with impression material. However, these are not entirely satifactory as movement is not entirely eliminated and since an additional step is required in the impression procedure. In an impression tray available from Premier Dental Products Co. of Norristown, Pa., and illustrated in U.S. Pat. Nos. Des. 266,269 and 277,605, a series of vertically extending ribs are formed in the tray wall which at least to some extent inhibit lateral spreading of the impression material along the tray wall. However, the impression material still tends to separate from the wall and move inwardly into the tray as well as lift out of the tray when the teeth are removed from the impression material.

SUMMARY OF THE INVENTION

It is an object of the present invention to provide a new and improved dental impression tray which overcomes the above-described disadvantages of conventional dental impression trays.

Another object of the present invention is to provide a new and improved dental impression tray by which a more accurate impression of the dentition can be obtained than has been possible heretofore.

A particular object of the present invention is to provide a new and improved dental impression tray wherein separation of the soft impression material from the tray-defining wall and movement inwardly into the tray during and after the impression procedure is prevented to provide a more accurate impression of the dentition.

Another particular object of the present invention is to provide a new and improved dental impression tray wherein lifting of the soft impression material from the tray after the impression is taken is prevented to provide a more accurate impression of the dentition.

Briefly, in accordance with the present invention, these and other objects are obtained by providing a dental impression tray including a tray portion adapted to be loaded with impression material and which is anatomically contoured to fit over at least a part of a patient's upper and/or lower dentition, and wherein the tray portion includes a wall on which means are provided for preventing substantial inward and/or upward movement of the impression material situated in the region of the tray portion wall.

In the illustrated embodiment, a plurality of vertically extending adjacent ribs are integrally formed on the tray wall to define a plurality of channels between them into which the impression material flows. The ribs are configured so that the channels prevent the impression material from separating from the side wall in the inward direction. Each rib is also provided with surface means situated within the tray portion which prevents the impression material from lifting out of the tray when the teeth are removed from the impression material.

DESCRIPTION OF THE DRAWINGS

A more complete appreciation of the present invention and many of the attendant advantages thereof will be readily understood by reference to the following detailed description when considered in connection with the accompanying drawings in which:

FIG. 1 is a perspective view of one embodiment of a dental impression tray constructed in accordance with the invention;

FIG. 2 is a top plan view of the dental impression tray illustrated in FIG. 1 in the direction of arrows 2—2 of FIG. 1;

FIG. 3 is a section view taken along line 3—3 of FIG. 2;

FIG. 4 is a top plan view of the dental impression tray illustrated in FIGS. 1-3 loaded with soft impression material immediately prior to an impression being taken;

FIG. 5 is a section view taken along line 5—5 of FIG. 4 showing the dental impression tray in use;

FIG. 6 is a section view taken along line 6—6 of FIG. 5;

FIG. 7 is a section view taken along line 7—7 of FIG. 6;

FIG. 8 is a top plan view of the dental impression tray after the impression procedure has been completed; and FIG. 9 is a top plan view of another embodiment of a dental impression tray constructed in accordance with the invention.

DESCRIPTION OF THE PREFERRED EMBODIMENTS

Referring now to the drawings wherein like reference characters designate identical or corresponding parts throughout the several views, and more particularly to FIGS. 1-3, a dental impression tray, generally designate a 10, is illustrated which is adapted for use in obtaining an impression of the posterior or bicuspid and molar part of both the upper and lower dentitions. It is understood that other configurations for obtaining impressions of other areas of the dentition are within the scope of the invention. The tray 10 includes a tray portion 12 to which a handle 14 is connected. The tray portion 12 and handle 14 are integrally molded of suitable plastic material, such as polyvinyl chloride or polyethylene.

Tray portion 12 includes an inner or lingual wall 16, an outer or buccal wall 18 and a bridging arm 20 interconnecting the inner and outer walls 16 and 18. As best seen in FIGS. 2 and 6, the inner and outer walls 16 and 18 are contoured to follow the anatomical configuration of the bicuspid and molar areas and so that, when properly positioned, the bicuspid and molar areas of both of the upper and lower dentitions of which an impression is to be obtained will fit within the tray portion between the walls with correct interdigitation of the teeth. Each wall has a height which smoothly decreases from a maximum at its central region to a minimum at its end regions as best seen in FIGS. 1 and 3. A web 22 formed of any suitable material, such as gauze, extends horizontally through the tray portion 12 at the mid-height thereof and separates the latter into upper and lower tray portions 12a and 12b (FIGS. 3 and 5) for receiving the upper and lower dentition parts respectively. The web is preferably assembled as part of the tray 10 during the molding operation and forms a common bottom for each of the upper and lower tray portions.

In use, any suitable conventional elastomeric impression material is prepared and one or both of the upper and lower tray portions 12a and 12b are loaded with the impression material while in a soft condition. The loaded tray is then grasped by handle 14 and situated opposite to the dentition area whereupon the patient bites into the soft impression impression material to form an impression of the dentition in the material. The patient's jaw is opened to remove the teeth from the impression material leaving an impression of the dentition. The impression material is allowed to set whereupon it is used as a mold for making a model.

The construction of the dental impression tray and its use as described above is conventional. As noted, conventional dental impression trays have the disadvantage that as the patient bites into the soft impression material and then removes his teeth from the material after the impression is obtained, the impression material tends to separate from the walls 16 and 18 and move inwardly into the tray portions and laterally along the respective walls. Moreover, the impression material tends to lift out of the tray portions as the patient opens his jaw. This detracts from the accuracy of the impression obtained during the procedure and it is the object of the invention to eliminate such movement and thereby improve the quality of the impression.

In accordance with the invention, a plurality of vertically extending ribs 24 are integrally formed on the walls 16 and 18 in closely spaced adjacent relationship with each other, each rib 24 extending into a respective one of the tray portions 12a and 12b from substantially the vertical edge region of a respective wall. The inner end of each rib 24 terminates at an inner end surface 26 (FIGS. 3, 5 and 7) which is substantially horizontal and vertically spaced from the web 22 for reasons which will become clear hereinbelow. The ribs 24 define a plurality of channels 28 between them, each channel being bounded by side surfaces 24a of adjacent ribs 24 and the inner surface of a respective one of the walls 16 and 18.

Referring to FIGS. 2 and 6, the ribs 24 are formed with a dovetail-shaped cross-section so that the channels 28 defined between them narrow or converge in the inward direction, i.e., towards the interior of the tray portions 12a and 12b. Thus, each side surface 24a of each rib 24 constitutes an undercut surface and the throat or opening of each channel 28 has a reduced lateral dimension with respect to the lateral dimensions of the remainder of that channel.

Thus, in use, one or both of the upper and lower tray portions 12a and 12b are loaded with soft impression material 30 as seen in FIG. 4 and the loaded tray portions are manipulated into position opposite the desired dentition part of which the tray is adapted to obtain an impression. The patient then bites into the soft impression material as seen in FIG. 5. This causes the impression material to flow into and substantially fill the channels 28 as seen in FIG. 6. The impression material 30 is also caused to flow under the inner end surfaces 26 of ribs 24 as seen in FIGS. 5 and 7. The patient opens his jaw to withdraw the teeth from material 30 leaving impressions 32 (FIG. 8) therein. The material 30 is allowed to set and can be used as a mold for a model of the dentition.

By virtue of the undercuts presented by the side surfaces 24a of ribs 24 and the diminished throat region of channels 28, the impression material which flowed into the channels as the impression was taken will be held therein and prevented from separating from the wall 16 and 18, i.e., inward movement into the tray portions will be prevented. This has the consequent effect of maintaining the impression material which is contiguous to the material situated within channels 28 in place thereby improving the accuracy of the impression. The presence of ribs 24 also prevents the impression material from flowing or spreading laterally along the walls as will be readily understood. Moreover, the impression material 30 adjacent to the walls 16 and 18 cannot be lifted out of the tray when the patient withdraws his teeth from the impression material by virtue of the presence of the horizontal end surfaces 26 of ribs 24. Thus, the impression material 30 has flowed into contiguity with surfaces 26 so that the surfaces 26 present an obstacle to the impression material moving vertically out of the tray portion. The impression material located within the channels 28 is also prevented from being lifted out of the tray portions by the forces of adhesion with the material situated contiguously with surfaces 26. In the manner described above, the impression material is held in position and is prevented from movement both during and after the impression procedure thereby improving the accuracy of the impression obtained.

The invention may be applied in the construction of dental impression trays for taking impressions of other parts of dentition. Referring to FIG. 9, another embodiment of a dental impression tray in accordance with the invention, generally designated 40, is illustrated which is adapted for use in obtaining an impression of the anterior or cuspid-to-cuspid part of both the upper and lower dentitions. The tray 40 includes a tray portion 42 to which a handle 44 is connected. The tray portion 42 includes an outer or buccal wall 48, an inner wall 50 having a U-shape opposite outer wall 48 and a web 52 separating the tray portion into upper and lower tray portions as in the case of the previously described embodiment. A plurality of ribs 54 having dovetail cross-sections are formed on the outer wall 48 and are provided with inner horizontal end surfaces (not shown) similar to surfaces 26 of the previously described embodiment. Other configurations of dental impression trays in accordance with the invention are still possible, such as for obtaining an impression of a complete quadrant of the dentition.

Obviously, numerous modifications and variations of the invention are possible in the light of the above teachings. For example the undercut surfaces which prevent inward separation of the impression material from the tray portion-defining wall may be provided by constructions other than ribs. The ribs may be provided with only a single undercut side surface, although the illustrated embodiment is preferred. Similarly, the lifting movement of the impression material may be prevented by horizontal surfaces provided by other constructions than the end surfaces of the ribs. The invention may be applied to dental impression trays wherein an impression can be obtained of only a single one of the upper or lower dentition parts at one time. It is also understood that a tray in accordance with the invention can be provided with means for preventing inward movement of the impression material without means for preventing upward movement and vice versa. Accordingly it is to be understood that within the scope of the claims appended hereto, the invention may be practiced otherwise than as specifically disclosed herein.

What is claimed is:

1. A dental impression tray for use in obtaining an impression of at least a part of a dentition, comprising: a tray portion adapted to be loaded with impression material, said tray portion being anatomically contoured to fit over at least a part of a patient's upper and/or lower dentition, said tray portion including at least one wall on which first surface means are formed for preventing substantial inward movement of impression material situated in the region of said tray portion wall into said tray portion, said first surface means comprising a plurality of ribs formed on said tray portion wall, each rib including at least one undercut surface.

2. The combination of claim 1 wherein said plurality of ribs include a plurality of adjacent ribs defining a plurality of channels therebetween whereby when an impression is taken, the impression material flows into said channels.

3. The combination of claim 2 wherein each of said ribs has at least one undercut side surface.

4. The combination of claim 2 wherein each of said ribs has a substantially dovetail-shaped cross-section and wherein each of said channels converge in an inward direction into said tray portion.

5. The combination of claim 4 wherein said tray portion includes a bottom and wherein said ribs have an inner end comprising a substantially horizontal inner end surface which is spaced from said tray portion bottom.

6. The combination of claim 1 wherein said tray portion includes a bottom and wherein said ribs have an inner end comprising a substantially horizontal inner end surface which is spaced from said tray portion bottom.

7. A dental impression tray for use in obtaining an impression of at least a part of a dentition, comprising: a tray portion adapted to be loaded with impression material, said try portion being anatomically configured to fit over at lesat a part of a patient's upper and/or lower dentition, said tray portion including at least one wall on which horizontal surface means are formed for preventing substantial vertical movement of the impression material situated in the region of said wall out of said tray portion, said horizontal surface means including a plurality of ribs formed on said tray portion wall, each rib having an inner end comprising a substantially horizontal inner end surface, and wherein said ribs include undercut surface means for preventing substantial inward movement of impression material situated in the region of said tray portion wall into said tray portion.

8. A dental impression tray for use in obtaining an impression of at least a part of a dentition, comprising: a tray portion adapted to be loaded with impression material, said tray portion being anatomically configured to fit over at least a part of a patient's upper and/or lower dentition, said tray portion including at least one wall on which horizontal surface means are formed for preventing substantial vertical movement of the impression material situated in the region of said wall out of said tray portion, said horizontal surface means including a plurality of ribs formed on said tray portion wall, each rib having an inner end comprising a substantial horizontal inner end surface, each rib further having a substantially dovetail-shaped cross-section defining at least one undercut surface, wherein said ribs form channels between them which converge in an inward direction into said tray portion, said undercut surface comprising means for preventing substantial inward movement of impression material situated in the region of said tray portion wall into said tray portion.

9. A dental impression tray for use in obtaining an impression of at least a part of a dentition, comprising: a tray portion adapted to be loaded with impression material, said tray portion being anatomically contoured to fit over at least a part of a patient's upper and/or lower dentition, said tray portion including at least one wall on which first surface means are formed for preventing substantial inward movement of impression material situated in the region of said tray portion wall into said tray portion, said first surface means comprising a plurality of channels formed on said tray portion wall, each channel having a mouth opening into said tray portion, and each channel converging in an inward direction towards said mouth thereof.

* * * * *